(12) United States Patent
Pirkle et al.

(10) Patent No.: US 10,724,968 B2
(45) Date of Patent: Jul. 28, 2020

(54) SYSTEM AND METHOD FOR SOLUTION CONSTITUENT AND CONCENTRATION IDENTIFICATION

(71) Applicant: Battelle Memorial Institute, Columbus, OH (US)

(72) Inventors: Wesley C. Pirkle, New Albany, OH (US); Richard L. Shoaf, Westerville, OH (US)

(73) Assignee: Battelle Memorial Institute, Columbus, OH (US)

(*) Notice: Subject to any disclaimer, the term of this patent is extended or adjusted under 35 U.S.C. 154(b) by 0 days.

(21) Appl. No.: 16/428,419

(22) Filed: May 31, 2019

(65) Prior Publication Data

US 2019/0285556 A1   Sep. 19, 2019

Related U.S. Application Data

(63) Continuation-in-part of application No. 16/273,617, filed on Feb. 12, 2019, now Pat. No. 10,663,411,
(Continued)

(51) Int. Cl.
| | |
|---|---|
| *G01N 22/00* | (2006.01) |
| *G01N 29/024* | (2006.01) |
| *G01N 33/15* | (2006.01) |
| *G01N 29/032* | (2006.01) |
| *G01N 29/28* | (2006.01) |
| *G01N 29/32* | (2006.01) |
| *G01N 29/44* | (2006.01) |

(Continued)

(52) U.S. Cl.
CPC ............... *G01N 22/00* (2013.01); *A61J 1/10* (2013.01); *G01N 29/024* (2013.01); *G01N 29/032* (2013.01); *G01N 29/28* (2013.01); *G01N 29/326* (2013.01); *G01N 29/4436* (2013.01); *G01N 33/15* (2013.01); *G06K 7/10366* (2013.01); *G06K 7/1413* (2013.01); *A61J 2205/10* (2013.01); *A61J 2205/30* (2013.01); *A61J 2205/60* (2013.01); *G01N 2291/011* (2013.01); *G01N 2291/015* (2013.01); *G01N 2291/022* (2013.01)

(58) Field of Classification Search
CPC ....................................................... G01N 22/00
See application file for complete search history.

(56) References Cited

U.S. PATENT DOCUMENTS

| | | |
|---|---|---|
| 4,767,982 A | 8/1988 | Florig et al. |
| 6,833,540 B2 | 12/2004 | MacKenzie et al. |
| (Continued) | | |

FOREIGN PATENT DOCUMENTS

| | | |
|---|---|---|
| WO | 90/04167 A1 | 4/1990 |
| WO | 2013/033162 A1 | 3/2013 |

OTHER PUBLICATIONS

International Search Report and Written Opinion in International Application No. PCT/US14/61252, dated Apr. 1, 2015 (17 pages).

*Primary Examiner* — Manuel A Rivera Vargas
(74) *Attorney, Agent, or Firm* — Benesch, Friedlander, Coplan & Aronoff LLP

(57) ABSTRACT

A system and method are disclosed for determining a constituent and/or concentration of a solid dissolved in a liquid. In one embodiment, a method is provided to interrogate and identify a liquid in a medical container.

18 Claims, 15 Drawing Sheets

Related U.S. Application Data which is a continuation of application No. 15/128,027, filed as application No. PCT/US2014/061252 on Oct. 17, 2014, now Pat. No. 10,234,404.

(60) Provisional application No. 61/969,041, filed on Mar. 21, 2014.

(51) Int. Cl.
*A61J 1/10* (2006.01)
*G06K 7/14* (2006.01)
*G06K 7/10* (2006.01)

(56) References Cited

U.S. PATENT DOCUMENTS

| | | |
|---|---|---|
| 6,871,169 B1 | 3/2005 | Hazen et al. |
| 7,047,058 B1 | 5/2006 | Dvorsky et al. |
| 7,107,087 B2 | 9/2006 | Hwang et al. |
| 7,122,012 B2 | 10/2006 | Bouton et al. |
| 8,189,188 B2 | 5/2012 | Busch et al. |
| 8,295,920 B2 | 10/2012 | Bouton et al. |
| 8,996,338 B2 | 3/2015 | Xu et al. |
| 9,907,908 B2 | 3/2018 | Chen et al. |
| 10,168,305 B2 * | 1/2019 | Pirkle ............... G01N 29/02 |
| 2004/0229376 A1 * | 11/2004 | Beauducel ......... G01F 23/2845 436/164 |
| 2010/0026300 A1 * | 2/2010 | Klein ................. G01N 22/00 324/316 |
| 2012/0055253 A1 | 3/2012 | Sinha |
| 2013/0265190 A1 | 10/2013 | Mukherjee et al. |
| 2014/0225614 A1 | 8/2014 | Prado |
| 2014/0366626 A1 | 12/2014 | Kuroda et al. |
| 2015/0060673 A1 | 3/2015 | Zimdars |
| 2015/0276920 A1 | 10/2015 | Kim et al. |

\* cited by examiner

Maximum PLS and Next Closest

| Drug | Largest Average PLS | 2ndLargest PLS |
|---|---|---|
| Epinephrine | 0.27 (Norepinephrine) | 0.26 (Epinephrine) |
| Fentanyl | 0.16 (Fentanyl) | 0.13 (Midazolam) |
| Heparin | 0.13 (Heparin) | 0.12 (Phenylephrine) |
| Hydromorphone | 0.18 (Hydromorphone) | 0.17 (D5W) |
| Insulin | 0.94 (Insulin) | 0.05 (Oxytocin) |
| Magnesium Sulfate | 0.38 (Magnesium Sulfate) | 0.20 (Potassium Chloride) |
| Midazolam | 0.12 (Midazolam) | 0.11 (Phenylepherine) |
| Morphine | 0.77 (Morphine) | 0.28 (D5W) |
| Norepinephrine | 0.47 (Norepinephrine) | 0.28 (Epinephrine) |
| Oxytocin | 0.17 (Oxytocin) | 0.15 (Phenylephrine) |
| Phenylephrine | 0.33 (Phenylephrine) | 0.21 (Oxytocin) |
| Potassium Chloride | 0.72 (Potassium Chloride) | 0.10 (Magnesium Sulfate) |

FIG. 15

SYSTEM AND METHOD FOR SOLUTION CONSTITUENT AND CONCENTRATION IDENTIFICATION

CROSS-REFERENCE TO RELATED APPLICATIONS

This application is a continuation-in-part of application Ser. No. 16/273,617, filed on Feb. 12, 2019, which is a continuation of U.S. patent application Ser. No. 15/128,027, filed on Sep. 21, 2016, which is national stage entry of International Application No. PCT/US2014/061252, filed on Oct. 17, 2014, which claims priority from Provisional Patent Application No. 61/969,041, filed on Mar. 21, 2014, all of which are incorporated herein by reference in their entirety.

BACKGROUND

Systems and methods for screening and identifying liquid filled containers are known in the art and include systems and methods for detecting and distinguishing hazardous materials. For example, U.S. Provisional Application No. 61/892,138, filed on Oct. 17, 2013, now U.S. application Ser. No. 14/517,686 filed on Oct. 17, 2014, and assigned to Battelle Memorial Institute, which is incorporated by reference herein in its entirety, discloses a container screening system and method for detecting and distinguishing hazardous materials at airports using both radio frequency (RF) and ultrasonic (US) systems.

The ever increasing use of automation and technology in manufacturing requires use of automated quality control and assurance systems to prevent manufacturing defects and human error. Chemical and pharmaceutical manufacturing account for a large portion of worldwide manufacturing. The present application appreciates that identification of chemical and pharmaceutical solutions and compositions may be a challenging endeavor.

SUMMARY

In some embodiments, a system and/or method of identifying a constituent and a concentration of a solid dissolved in a solution contained in a container, includes providing an input radio frequency (RF) signal to the solution, receiving at least one of a reflected RF signal and a coupled RF signal, analyzing the received RF signal in at least one of a frequency domain and a time domain for a measurement to which a Partial Least Squares (PLS) regression has been applied, applying a first set of PLS functions to the received RF signal to determine a value of a constituent of the solid dissolved in the solution, applying a second set of PLS functions to the RF signal to determine a value of a concentration of the solid dissolved in the solution, comparing the value of the constituent and the value of the concentration against one or more baseline measurements in a database, and identifying the constituent and the concentration of the solid dissolved in the solution from the compared measurements.

The summary is provided merely for purposes of summarizing some example embodiments so as to provide a basic understanding of some aspects of the disclosure. Accordingly, it will be appreciated that the above-described examples should not be construed to narrow the scope or spirit of the disclosure in any way. Other examples, embodiments, aspects, and advantages will become apparent from the following detailed description taken in conjunction with the accompanying drawings.

BRIEF DESCRIPTION OF THE DRAWINGS

The accompanying figures, which are incorporated in and constitute a part of the specification, illustrate various example systems and methods, and are used merely to illustrate various example embodiments.

FIG. 15 is a chart of example averages for drugs using RF and PLS to identify the constituent of a solution.

DETAILED DESCRIPTION

Figure 1:
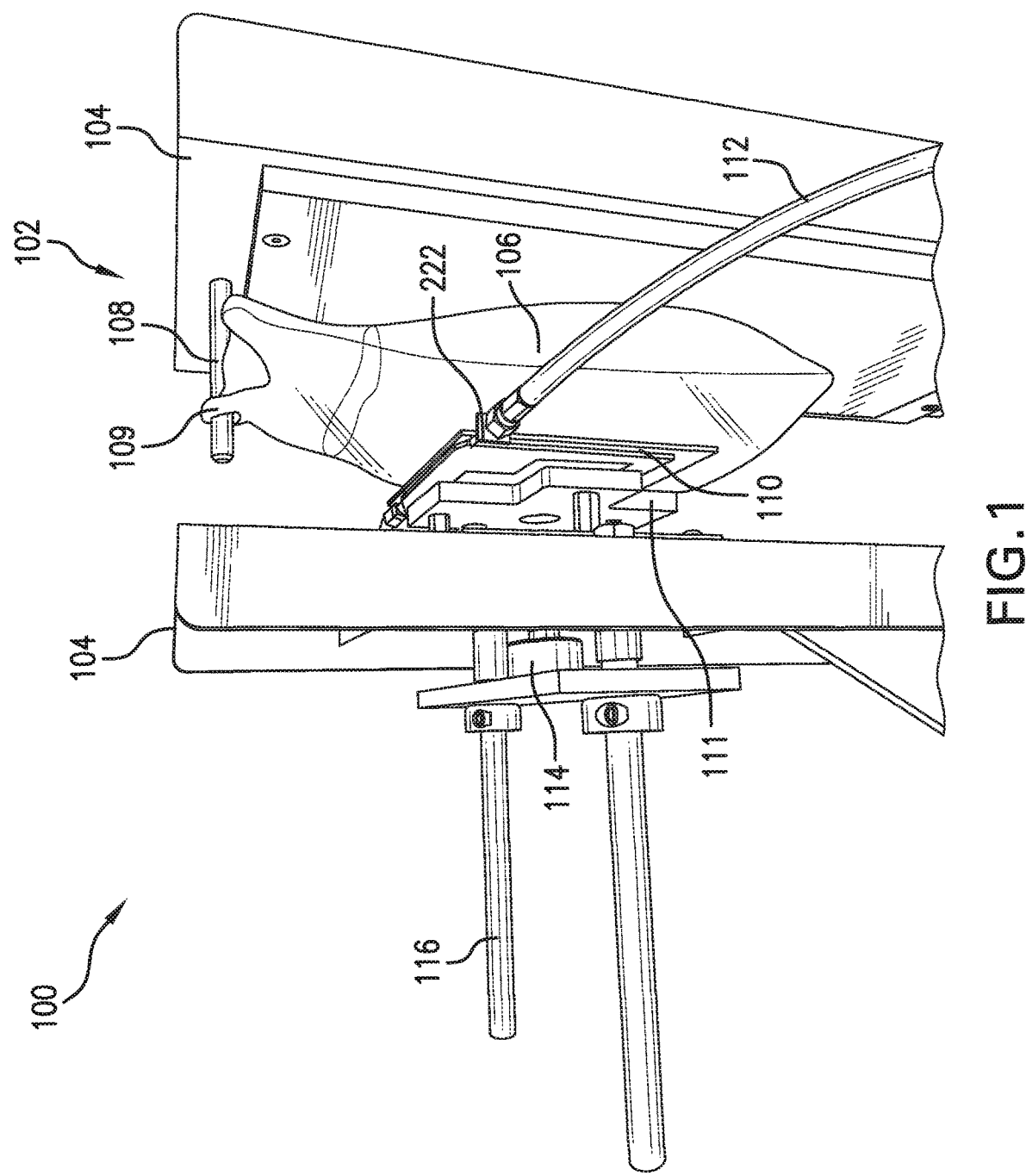
FIG. 1 illustrates a perspective view of an example embodiment of a liquid scanning system for IV drug verification and identification.

FIG. 1 illustrates a perspective view of an example embodiment of a liquid scanning system 100 for solution constituent and concentration identification. In some examples, the liquid scanning system 100 may be used to accurately identify the constituents and/or concentrations of pharmaceuticals and liquid solutions that have been placed in IV bags, syringes, and other containers used for holding liquid drug mixtures. In other examples, the liquid scanning system 100 may be used to identify the constituents and/or concentrations of other contents contained in liquid solutions, e.g., for identifying constituents and/or concentrations of contents dissolved in liquids at security checkpoints. For the sake of explanation, the liquid scanning system 100 is described for identifying contents of liquid solutions in IV bags or syringes.

The liquid scanning system 100 may include a test fixture 102 for conducting liquid scanning in a controlled, repeatable test environment. Test fixture 102 may include one or more vertical plates 104, between which a container with liquid sample 106 may be placed. One or more vertical plates 104 may have a container mounting hardware 108 thereon for affixing container with liquid sample 106. Container with liquid sample 106 may have a standardized feature 109 thereon to interface with container mounting hardware 108. In one embodiment, standardized feature 109 is an IV bag loop operable for use with a standardized IV bag stand or IV bag pole. Standardized feature 109 interfacing with container mounting hardware 108 may ensure consistent placement of container with liquid sample in test fixture 102. Test fixture 102 may also include mount 111 for attaching RF sensor 110 thereon. Mount 111 may provide a sturdy attachment point for RF sensor 110 to ensure that RF sensor 110 is repeatedly mounted in a same position in test fixture 102. RF sensor 110 may include an input and output jack 222 for attaching a wire 112. Wire 112 may be used to transmit an RF signal to input jack 222 for use with sensor 110 for interrogating container with liquid sample 106. In one embodiment, in place of RF sensor 110, a narrow-band or wide-band antenna (not shown) may be used for interrogating container with liquid sample 106. Wire 112 may also be used to transmit an output RF signal from output jack 222 to be analyzed by a processor or computing device (not shown). In one embodiment, wire 112 is a coaxial cable. An output RF signal may include a reflected RF signal or a coupled RF signal. RF sensor 110 may include one or more input and output jacks 222. In one embodiment, RF sensor may have one jack 222 designated as input jack 222 and may have one jack 222 designated as output jack 222. In another embodiment, jack 222 may be both input jack 222 and output jack 222. Input/output jack 222 may be a connection for connecting coaxial type cables. In a non-limiting example, input/output jack 222 may be a male/female BNC connector to interface with a corresponding connector on wire 112. In another non-limiting example, input/output jack 222 are one of: F-type connectors, N-type connectors, RF connectors, and UHF connectors which connector to a corresponding connection on wire 112 to secure wire 112 to input/output jack 222. Behind RF Sensor 110 and mount 111 may be a pressure sensor 114 to measure how much pressure is being exerted on container with liquid sample 106 by vertical plates 104. Pressure sensor 114 may interface with one or more control devices (not shown) to automatically adjust the pressure exerted by vertical plates 104 on container with liquid sample 106. In one embodiment, pressure sensor 114 on detecting a certain pressure may output a detected pressure to a control device or processor (not shown) to control an electric motor (not shown) to automatically move vertical plate 104 back and forth along cylinder slide 116 relative to detected pressure from pressure sensor 114.

Figure 2:
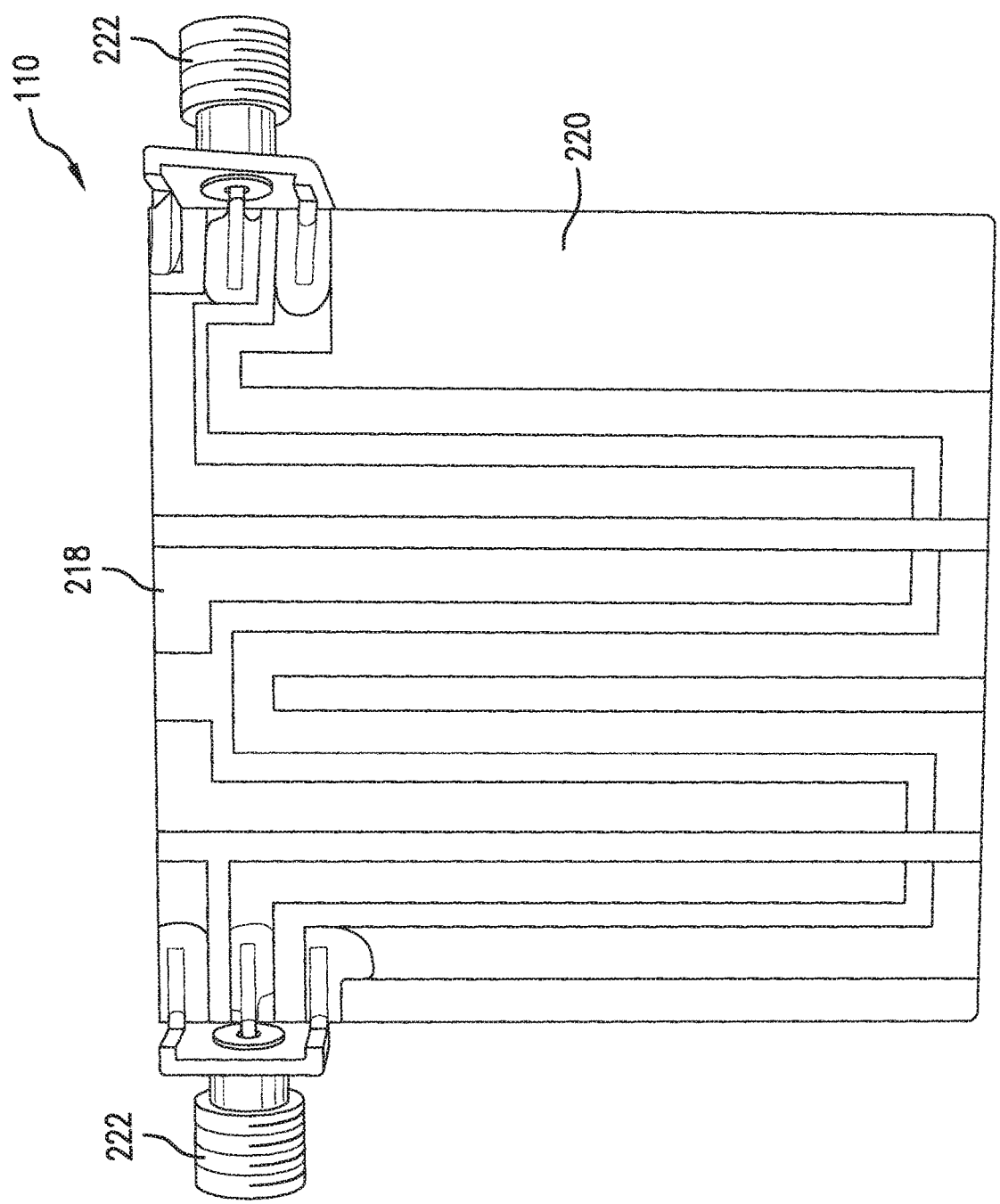
FIG. 2 illustrates a perspective view of an example RF sensor.

Referring to FIG. 2, perspective view of an example RF sensor 110 is illustrated. RF sensor 110 may be used to sense an output RF signal such as a reflected output signal or a coupled output signal. Output RF signal may result from a transmitted RF input signal reflecting off of container with liquid sample 106 and being received by RF sensor 110 to be output as an output RF signal. Output RF signal may result from a direct coupled input signal interacting with container with liquid sample 106 to provide a coupled output RF signal to RF sensor 110. RF sensor may include a conductive trace 218 on non-conducting substrate 220. Conductive trace 218 may be used to conduct and carry both an input and output RF signal to input and output jacks 222. In one embodiment, conductive trace 218 touches container with liquid sample 106 to produce a coupled RF output signal carried on conductive trace 218 to output jack 222. Output jack 222 may further convey coupled RF output signal to wire 112 such that RF signal can be further transmitted to a processor or computer for further signal processing and analysis. In one embodiment, sensor 110 is used in addition to transmitted RF signals from one or more antennas (not shown) to interrogate container with liquid sample 106. In this embodiment, compared to antennas, sensor 110 will not emit much, if any, RF energy. Antennas for transmitting and receiving RF signals may include wide band antennas and narrow band antennas.

Figure 3:
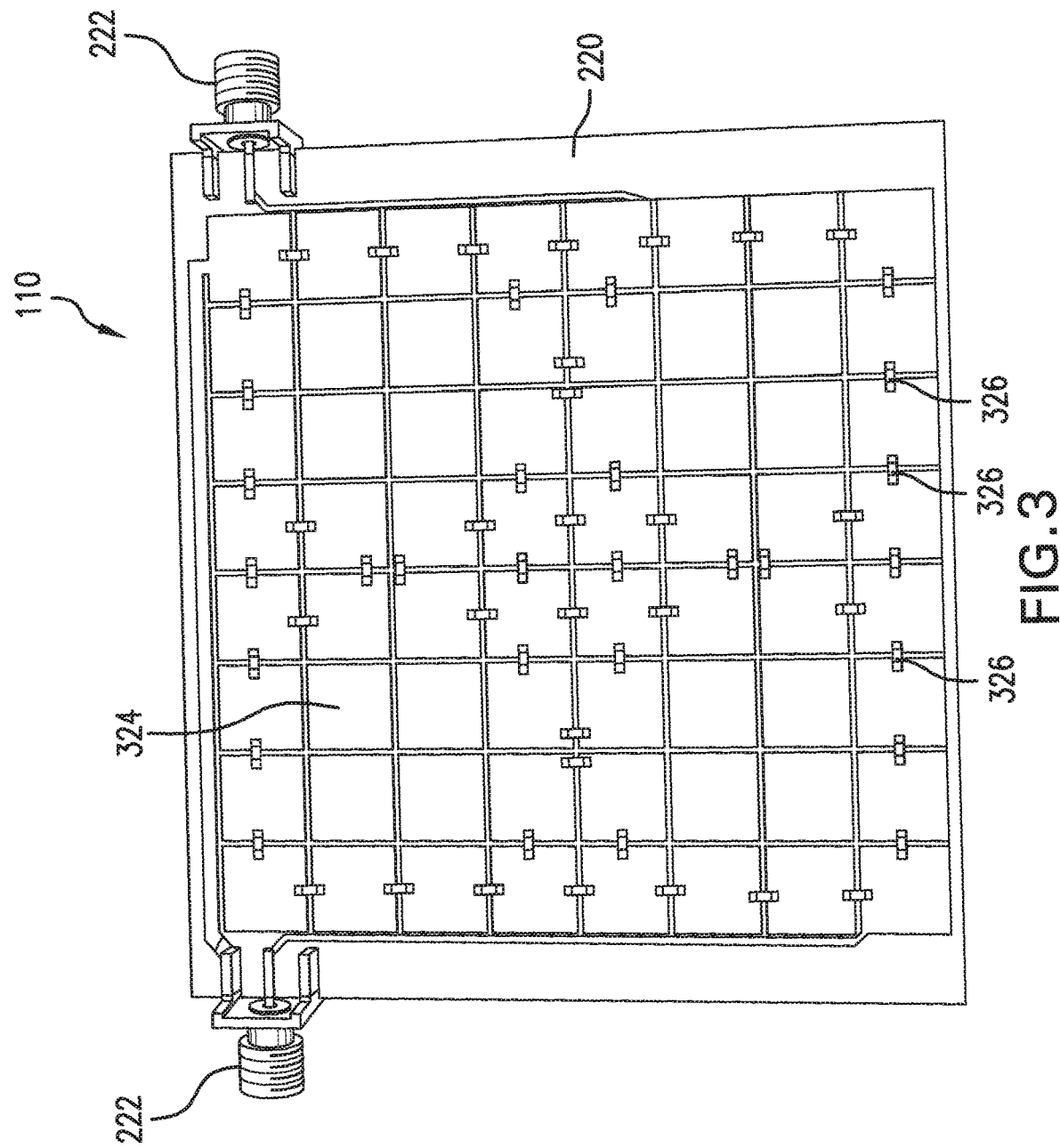
FIG. 3 illustrates a perspective view of an example RF sensor.
Figure 4:
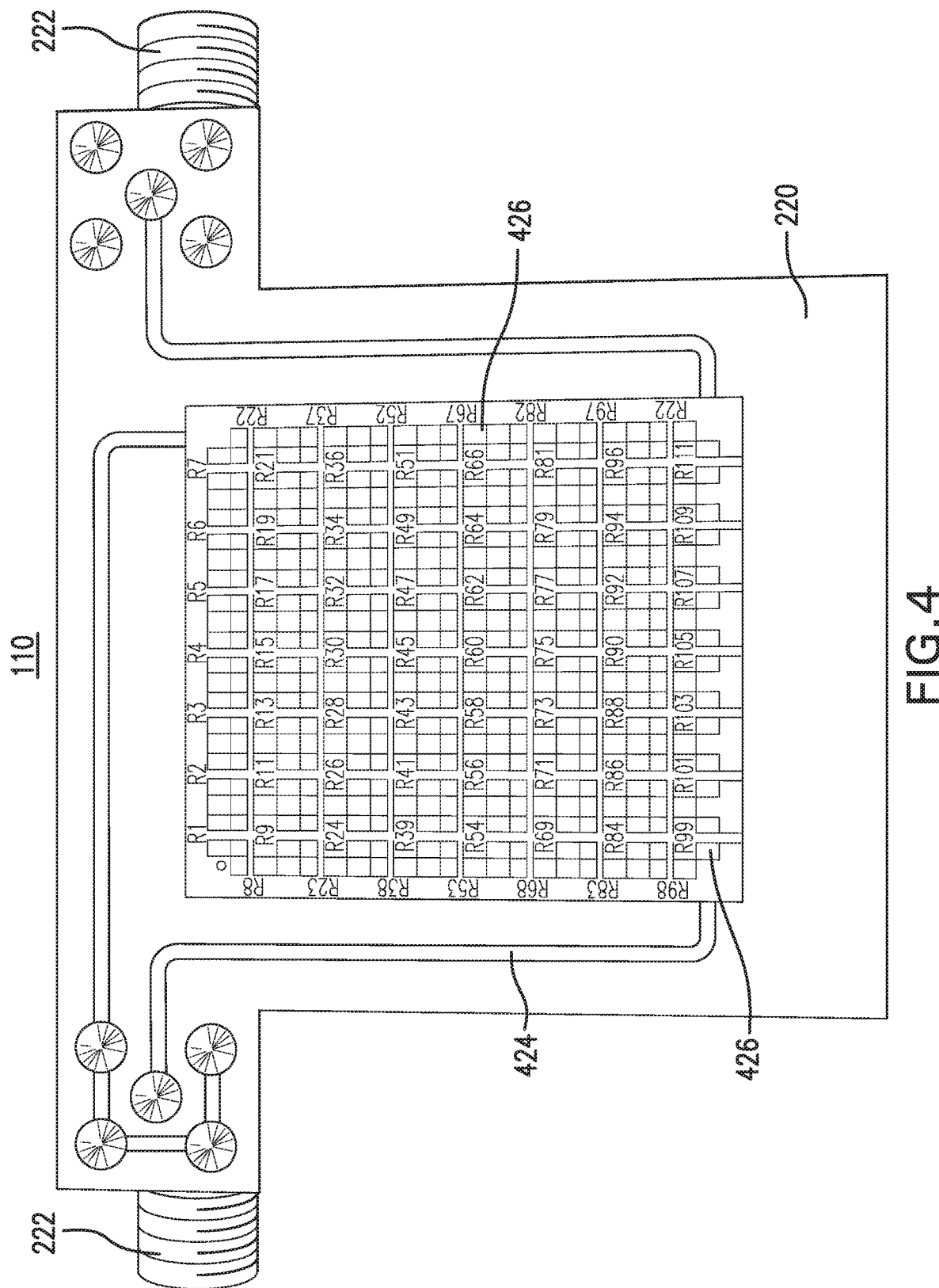
FIG. 4 illustrates a perspective view of an example RF sensor.

Referring to FIGS. 3 and 4, perspective views of other example RF sensors 110 are illustrated respectively. RF sensor 110 may be used to sense an output RF signal such as a reflected output signal or a coupled output signal. Output RF signal may result from a transmitted RF input signal reflecting off of container with liquid sample 106 and being received by RF sensor 110 to be output as an output RF signal. Output RF signal may result from a direct coupled input signal interacting with container with liquid sample 106 to provide a coupled output RF signal to RF sensor 110. With reference to FIG. 3, RF sensor 110 may be a grid array of diodes 326 arranged on a matrix of conductive portions 324. Conductive portions 324 may be separated by non-conducting substrate 220 and some of conductive portions 324 may be interconnected by diodes 326. Since diodes 326 only allow current to pass in one direction, RF signal will be routed through sensor 110 in a particular pattern or direction. Diodes in diode array of RF sensor 110 may be arranged based on required operating parameters of RF sensor 110. Similarly, with reference to FIG. 4, RF sensor may be a grid array of resistive elements 426 arranged on a matrix of conductive portions 424. Conductive portions 424 may be separated by non-conducting substrate 420 and some of conductive portions 424 may be interconnected by resistive elements 426. In one embodiment, resistive elements 426 are resistors. RF sensor 110 may include one or more input and output jacks 222. Again, a same input jack 222 may also be used as an output jack 222 for inputting and outputting an RF signal.

RF signals output by output jack 222 may be further conveyed via wire 112 to a processor or computer (not shown) for further signal processing. Both input and output RF signals may be further analyzed and processed by a computer, processor, and other like systems. RF signals may be analyzed in both a time and frequency domain. In one embodiment, a fast Fourier transform (FFT), discrete Fourier transform (DFT), or like algorithm may be used to convert an RF signal in a time domain to an RF signal in a frequency domain and vice-versa. RF signals may be analyzed by a computer or signal processor such as a digital signal processor (DSP) or spectrum analyzer. Input or output signal may be analyzed for a measurement of at least one or more S-parameters, a Q factor, a center frequency, a level of impedance match, a current, and a voltage drop. Measurements may also include a time domain measurement, a frequency domain measurement, a Fast Fourier Transform (FFT) ratio of two or more measurements, an FFT difference of two or more measurements, a measurement to which a time domain algorithm has been applied, and measurements to which a Partial Least Squares (PLS) regression has been applied. Measurements may be a real value, an imaginary value, a complex value, a magnitude, or a phase. In one embodiment, signals and measurements are processed and analyzed with computer hardware and software designed for such analysis, processing, computation, and comparison of such signals and measurements. In one embodiment, a computer running MATLAB® software is used to process and analyze signals, parameters and measurements. In another embodiment, a computer operatively connected to a memory or computer readable medium with baseline measurements thereon, is used to compare analyzed and processed signals, parameters, characteristic, and measurements against signals of known reference and baseline samples to provide an output which identifies, or reasonably predicts, an identity of a liquid sample based on similar characteristics, parameters, and measurements of known reference and baseline samples.

Liquid scanning system 100 may include either a temperature probe (not shown) or standoff probe (not shown) for determining a temperature of a container with liquid sample undergoing interrogation. Temperature measurements may be used to determine a temperature compensation factor which may be applied to known reference and baseline samples stored in a database. In one embodiment, liquid scanning system 100 may automatically apply a temperature compensation factor to known reference and baseline samples based on a temperature of container with liquid sample 106. In one embodiment, standoff probe for determining a temperature of a container with liquid sample undergoing interrogation is an infrared (IR) sensor.

Figure 5:
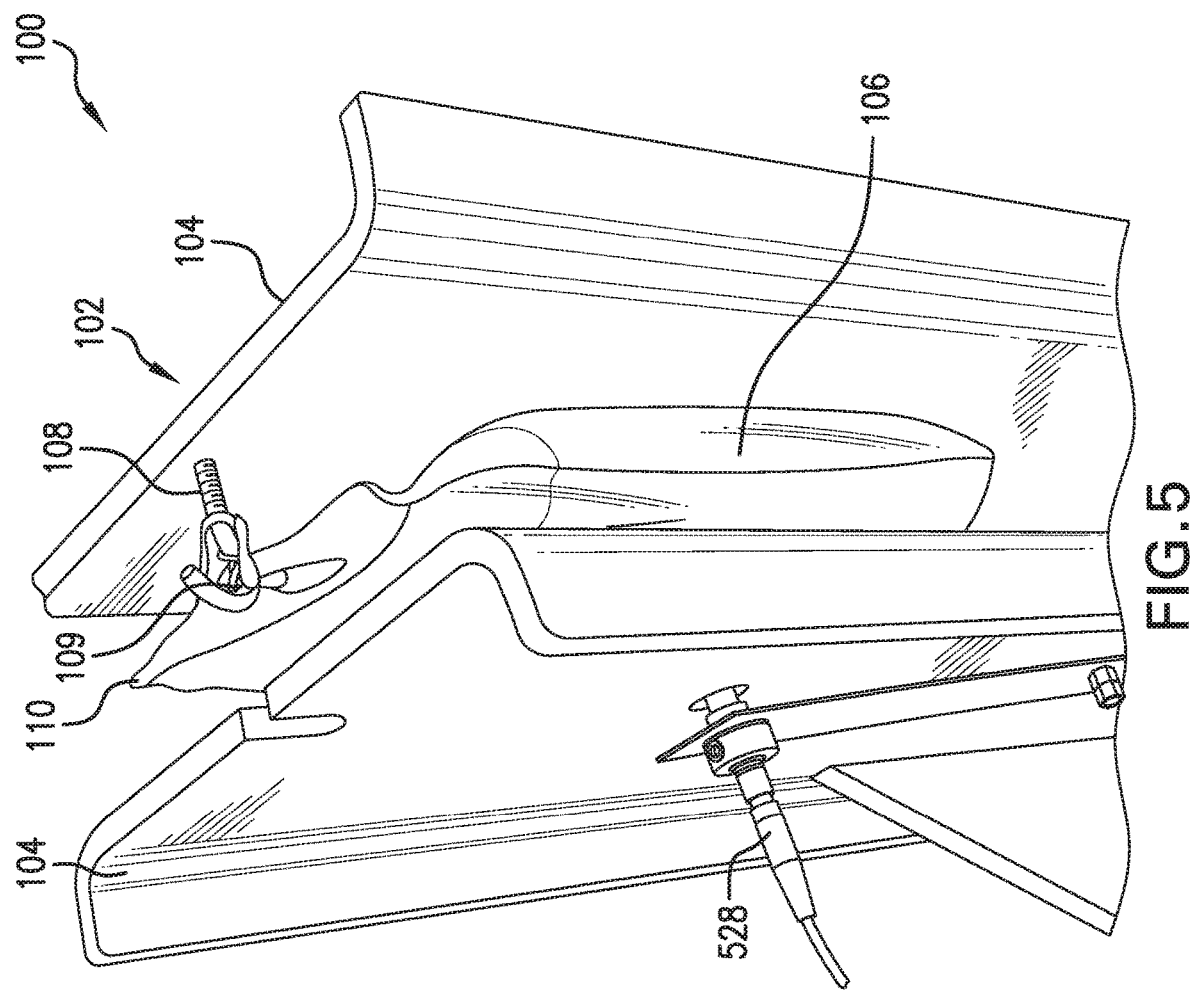
FIG. 5 illustrates a perspective view of an example embodiment of a liquid scanning system for IV drug verification and identification.

Referring to FIG. 5, a perspective view of an example embodiment of a liquid scanning system 100 for IV drug verification and identification is illustrated. In place of RF sensor 110 to provide an RF signal to container with liquid sample 106, FIG. 5 illustrates an example embodiment using an ultrasonic (US) device 528. US device 528 may be one of an US pulse generator that generates a high voltage signal for use by an US transducer, an US transducer for generating and receiving a pulse signal and echo pulse; an US transmitter for transmitting an US signal through container with liquid sample 106, or an US receiver for receiving a transmitted signal through a container with liquid sample 106. US device 528 may be coupled to container with liquid sample by one of a dry or liquid couplant (not shown) for better propagation of an US signal or pulse through container with liquid sample 106. US device 528 may also include one of an analog to digital converter (ADC) (not shown) for converting a received analog echo pulse or transmitted US signal to provide a better signal for analysis and processing. US device 528 may also use a delay line or delay circuit (not shown) to provide for better signal accumulation. Because of a velocity at which an US signal or pulse propagates through a medium and sample such as container with liquid sample 106, a delay line may be used to delay data collection from US transducer 528 and US receiver 528 to prevent unnecessary data collection. Test device 102 may also use pressure sensor 104 with US receiver 528 to provide a same pressure to container with liquid sample 106 for each test.

Figure 6:
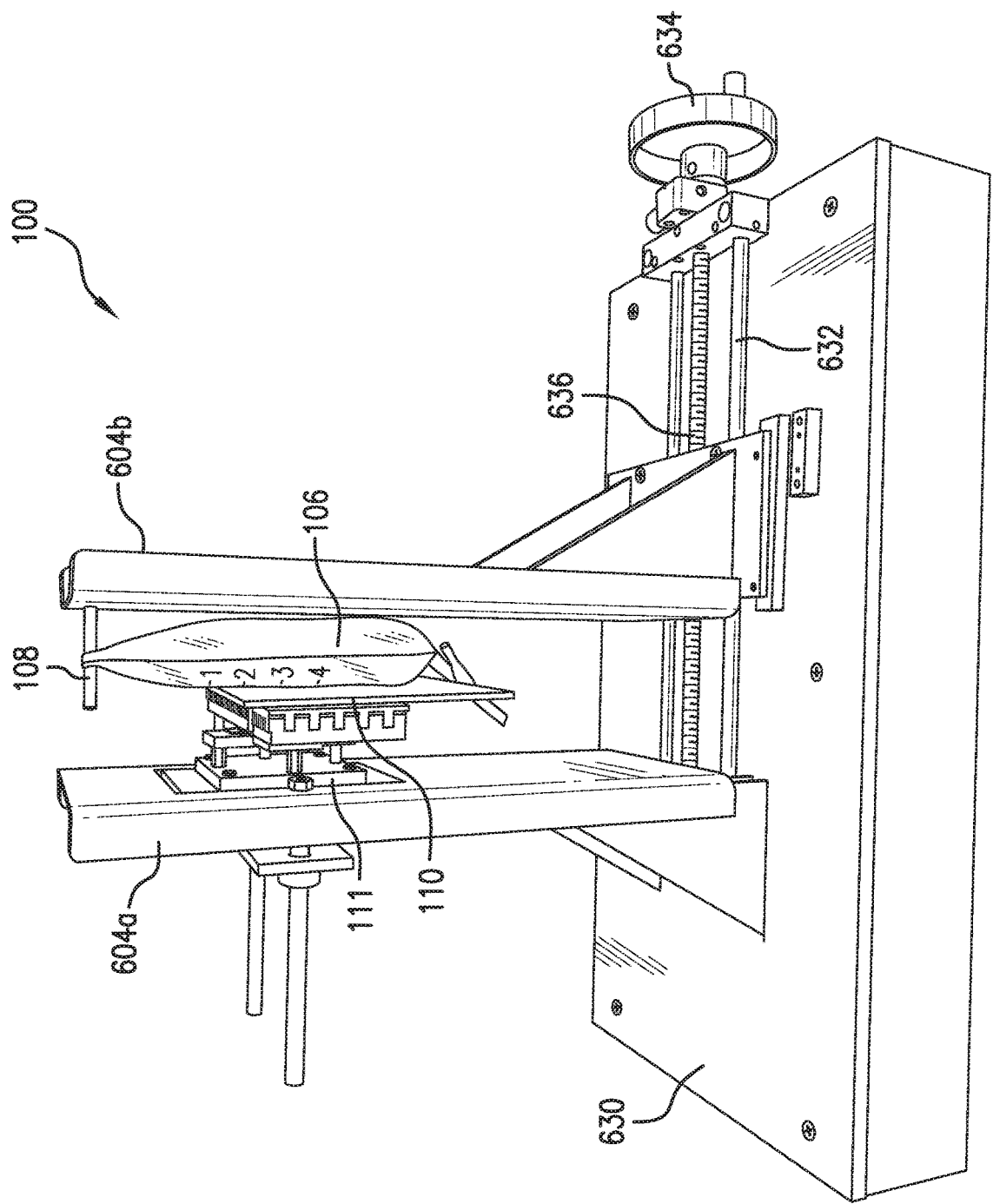
FIG. 6 illustrates a perspective view of an example embodiment of a liquid scanning system for IV drug verification and identification.

Referring to FIG. 6, a perspective view of an example embodiment of a liquid scanning system 100 for IV drug verification and identification is illustrated. Liquid scanning system 100 may include a test platform 630 upon which vertical plates 604a, 604b are operably connected. In one embodiment, one vertical plate 604a is immovably mounted to test platform 630 while another movable vertical plate 604b moves linearly toward and away from fixed, immovable vertical plate 604a. Movable vertical plate 604b may include hardware to affix movable vertical plate 604b to slider rails 632. Crank mechanism 634 may be operatively connected to linear driver 636, and linear driver 636 may be operatively connected to movable vertical plate 604b. Rotation of crank mechanism 634 may drive linear driver 636 to actuate movable vertical plate 604b towards and away from fixed vertical plate 604a depending on a direction of rotation of crank mechanism 634. For example, rotating crank mechanism 634 in a clockwise direction may move movable vertical plate 604b toward fixed vertical plate 604a. In one embodiment, linear driver 636 is a threaded rod. In another embodiment, linear driver 636 may be a linear actuator. Crank mechanism 634 may be replaced with an electric motor and various sensors may be employed to further automate and control movement of movable vertical plate 604b towards and away from fixed vertical plate 604a. Indicia (not shown) may be provided on test platform 630 to give a general length/distance measurements between fixed platform 604a and movable platform 604b, between RF sensor 110 and movable platform 604b, as well as providing an indication of a thickness of container with liquid sample 106. Measuring path length—that is, a thickness of container with liquid sample 106, may provide a path length distance measurement which may a necessary value for calculating an ultrasonic velocity. In one embodiment, a sensor (not shown) for sensing path length feeds sensed path length back into a control system to compensate/adjust for a desired path length and/or a desired pressure sensed by pressure sensor 114.

While liquid scanning system 100 for IV drug verification and identification has been illustrated with example test setups in a laboratory environment, test setups illustrated are non-limiting examples used to illustrate a utility of liquid scanning system 100. It is understood that liquid scanning system 100 may be packaged in a more commercially practical package. Such a commercial package may include all of the functionality of liquid scanning system 100 for IV drug verification and identification as described herein. In addition, a commercially packaged liquid scanning system 100 may be automated and further poka-yoked to assist an operator using liquid scanning system 100. For example, a commercial embodiment of systems described herein, may require an operator to insert an IV bag, syringe, or other container in a certain orientation (i.e. upright, lying flat, with a longitudinal axis orthogonal to RF sensor 110, etc.) before liquid scanning system 100 may be used to ensure a consistency of measurements.

Figure 7:
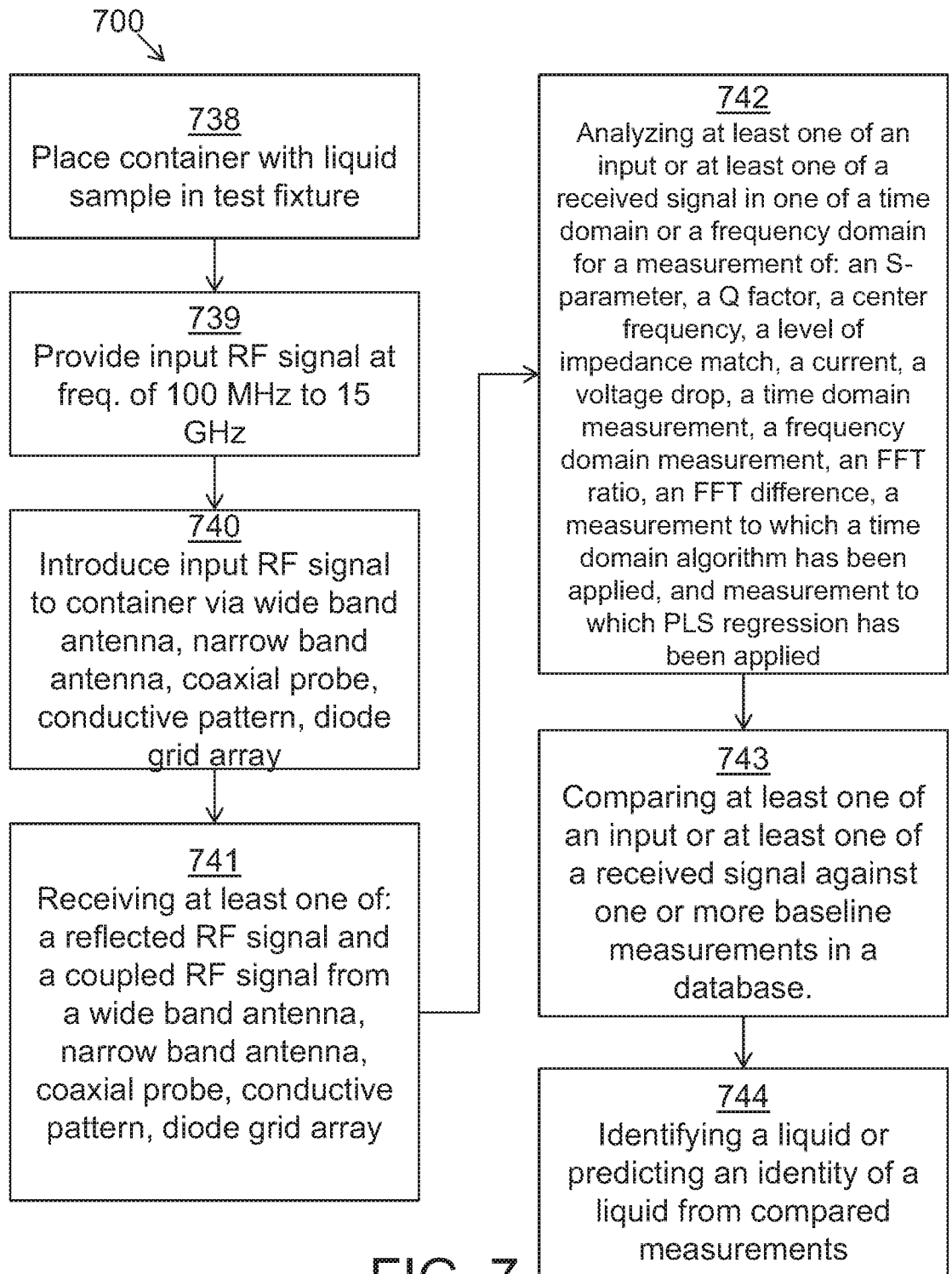
FIG. 7 illustrates a flow chart of an example method for using a liquid scanning system for IV drug verification and identification.

FIG. 7 is a flow chart of one embodiment of a method 700 for interrogating a liquid sample using an RF signal. In one embodiment, method 700 includes placing a container with a liquid sample in a test fixture (738). Method 700 also may include providing an input RF signal at a frequency between 100 MHz and 15 GHz (739). In one embodiment, input RF signal at a frequency between 100 MHz and 15 GHz is an RF signal with a fixed frequency between 100 MHz and 15 GHz. In another embodiment, input RF signal at a frequency between 100 MHz and 15 GHz is a frequency sweep with a varying frequency between 100 MHz and 15 GHz. Frequency sweep with a varying frequency between 100 MHz and 15 GHz may change frequency continuously from a set minimum frequency to a set maximum frequency or from a set maximum frequency to a set minimum frequency. In one embodiment, set minimum frequency is 100 MHz. In another embodiment, set maximum frequency is 15 GHz. Set minimum and maximum frequencies may be user defined. Frequency sweep may be at a defined rate, for example, 5 MHz/sec, 20 MHz/sec, 100 MHz/sec, and the like. Method 700 may also include introducing an RF signal to a container with a liquid sample by at least one of: one or more transmitting wide band antennas; one or more transmitting narrow band antennas; a coaxial probe providing an input RF signal; a conductive pattern (trace) providing an input RF signal; and a diode grid array providing an input RF signal (740). In one embodiment, antennas, coaxial probes, a conductive trace RF sensor, and a grid array RF sensor are all used in RF signal interrogation of a liquid sample. Method 700 may also include receiving at least one of a reflected RF signal and a coupled RF signal, at least one received signal generated from an introduction of an input RF signal to a container with a liquid sample, and received from at least one of: one or more receiving wide band antennas, one or more receiving narrow band antennas, a coaxial probe providing at least one of a reflected RF signal and a coupled RF signal; a conductive pattern providing at least one of a reflected RF signal and a coupled RF signal; and a grid array providing at least one of a reflected RF signal and a couple RF signal (741). Method 700 may also include analyzing at least one of an input RF signal and at least one of a received signal in at least one of a frequency domain or a time domain for a measurement of at least one of: an S-parameter (i.e. S11, S12, S21, S22), a Q factor, a center frequency, a level of impedance match, a current, and a voltage drop, wherein a measurement of at least one of an input RF signal and at least one of a received signal is one of a real value, an imaginary value, a complex value, a magnitude, and a phase (742). Method 700 may also include comparing at least one of an input or at least one of a received signal against one or more baseline measurements in a database (743). Method 700 may include identifying a liquid or predicting an identity of a liquid from compared measurements (744). Measurements may also include time domain and/or frequency domain measurements to which a Fast Fourier Transform (FFT) algorithm may be applied. An FFT may be applied to input RF signal measurements, received signal measurements, and other baseline measurements to provide transform values. Ratios and differences of FFT transform values may also be used to identify a liquid, and develop a liquid signature which may be stored in a database. Further time domain based algorithms may be applied to measurements to identify unknown liquids. Partial Least Squares (PLS) regression analysis of measurements, FFT transform value ratios, FFT transform value differences, and measurements to which time domain based algorithms have been applied may be used to generate regression values, and regression values may be used to identify a liquid.

In addition to using an RF signal to interrogate a liquid, method 700 may also include use of US interrogation to interrogate a liquid.

Figure 8:
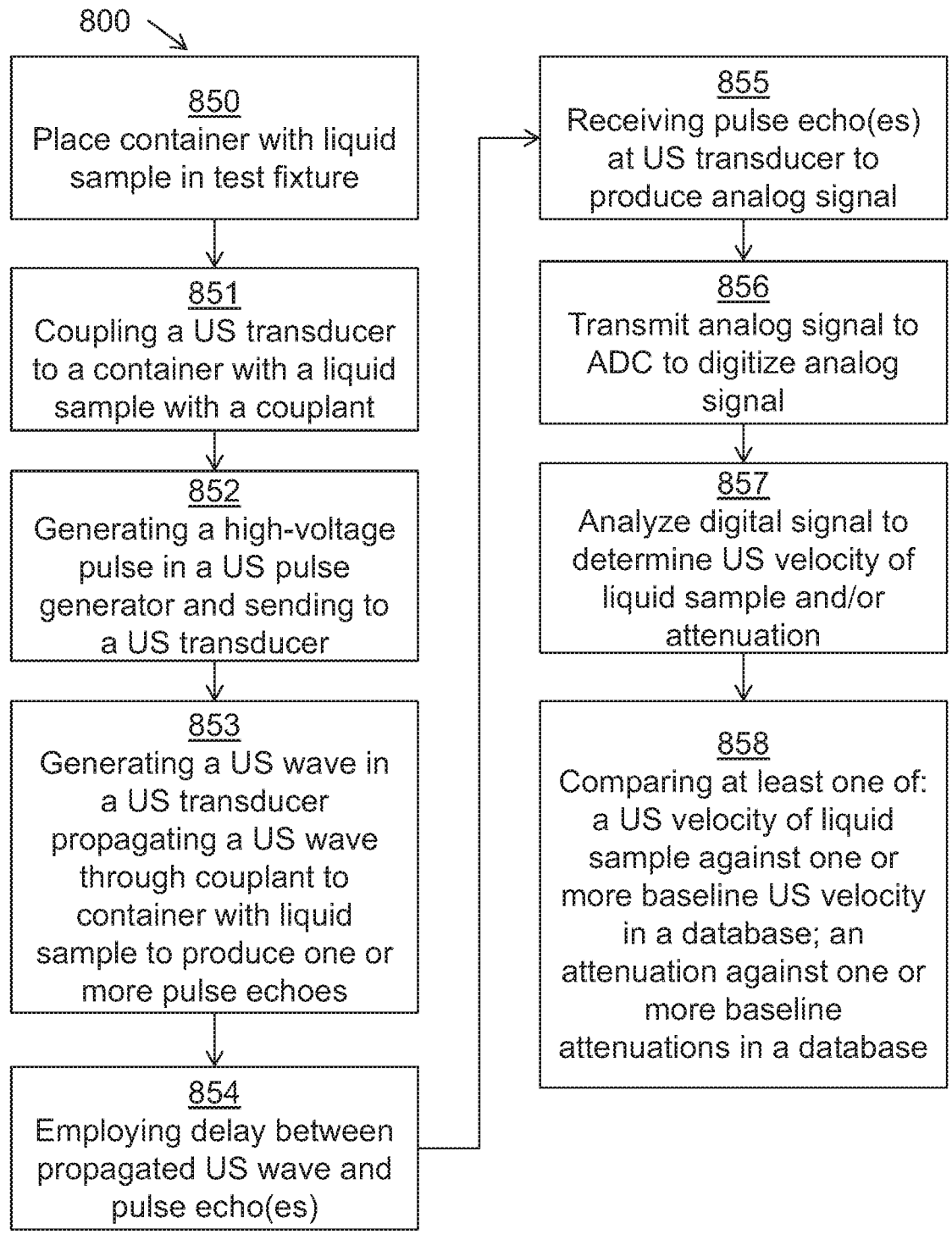
FIG. 8 illustrates a flow chart of an example method for using a liquid scanning system for IV drug verification and identification.

FIG. 8 is a flow chart of one embodiment of a method 800 for interrogating a liquid sample using an US pulse echo. Method 800 may include placing a container with a liquid sample in a test fixture (850). US transducer may be coupled to a container with a liquid sample in a test fixture with at least one of a liquid and solid couplant (851). A high-voltage pulse may be generated in a US pulse generator and sent from a US pulse generator to a US transducer (852). An US wave may be generated in a US transducer from a high-voltage pulse and propagated through a couplant to a container with a liquid sample to produce one or more pulse echoes to be received by an US transducer (853). A delay may be employed between a propagated US wave and one or more produced pulse echoes (854). One or more produced pulse echoes may be received at a US transducer to produce an analog signal (855). An analog signal may be transmitted to an analog to digital converter (ADC) to digitize a transmitted analog signal (856). A digitized signal may be analyzed to determine an US velocity of a liquid sample and/or attenuation of the one or more pulse echoes caused by the liquid sample (857). An US velocity of a liquid sample and/or an attenuation of the one or more pulse echoes caused by the liquid sample may be compared against one or more baseline US velocities and/or attenuations in a database, respectively, and a liquid may be identified or an identity of a liquid may be predicted from compared US velocities and/or attenuations (858). In addition to using a US pulse echo, method 800 may also include at least one of RF signal interrogation and US signal interrogation.

Figure 9:
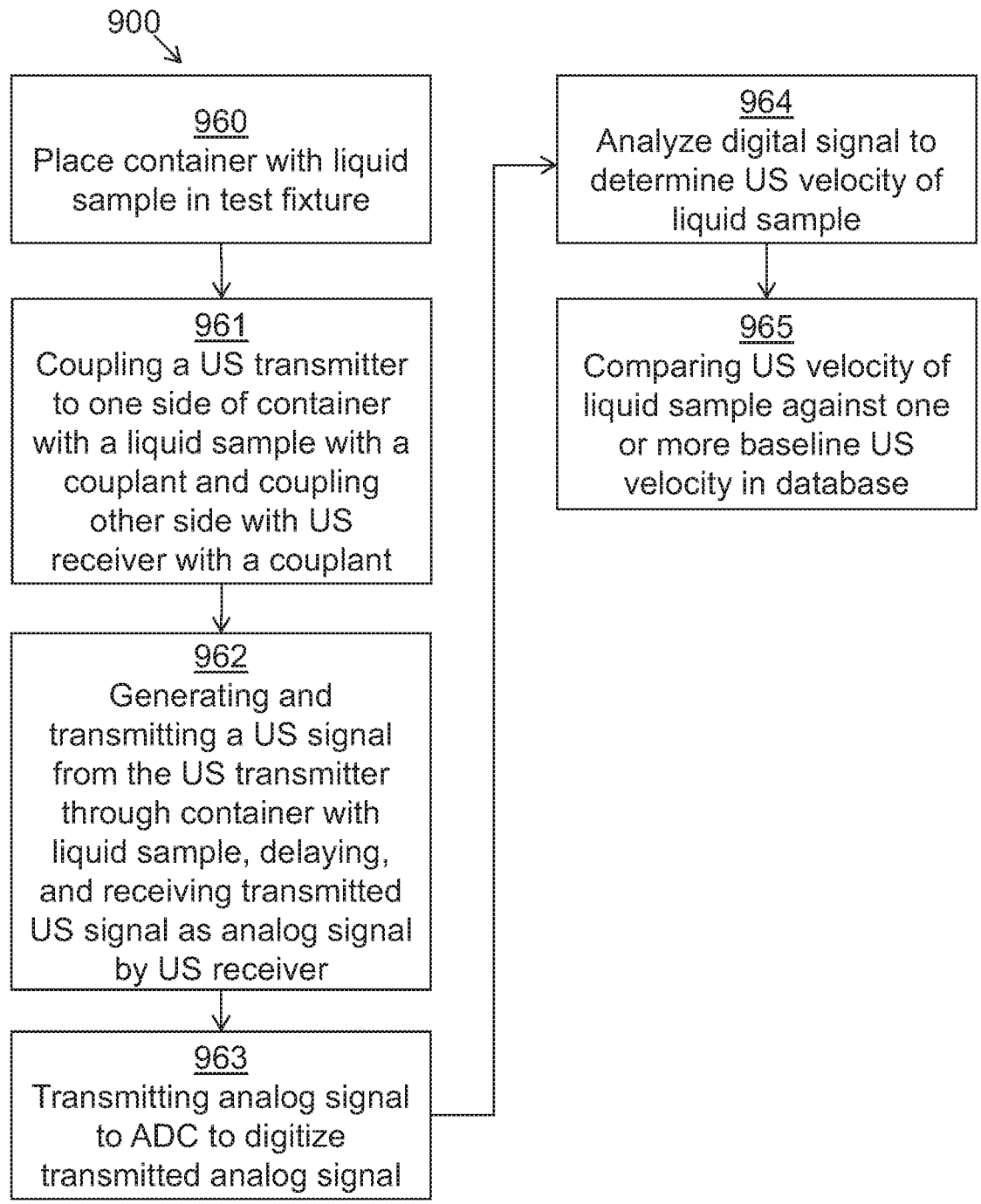
FIG. 9 illustrates a flow chart of an example method for using a liquid scanning system for IV drug verification and identification.

FIG. 9 is a flow chart of one embodiment of a method 900 for interrogating a liquid sample using an US signal. In one embodiment, method 900 may include placing a container with a liquid sample in a test fixture (960). At least one US transmitter with at least one couplant may be coupled to one side of a container with a liquid sample and an US receiver with at least one couplant may be coupled to another side of a container with a liquid sample (961). An US signal may be generated and transmitted from an US transmitter through a container with a liquid sample, and a delay may be employed after an US signal is transmitted, and before a transmitted US signal is received, and a transmitted US signal may be received as an analog signal at an US receiver on another side of a container with a liquid sample (962). An analog signal may be transmitted to an analog to digital converter (ADC) to digitize a transmitted analog signal (963). A digitized signal may be analyzed to determine an ultrasonic velocity of the liquid sample (964). An US velocity of a liquid sample may be compared against one or more baseline ultrasonic velocities in a database, and a liquid may be identified from ultrasonic velocities of known liquid signatures stored in the database, or an identity of an unknown liquid may be predicted based on compared ultrasonic velocities (965).

Figure 10:
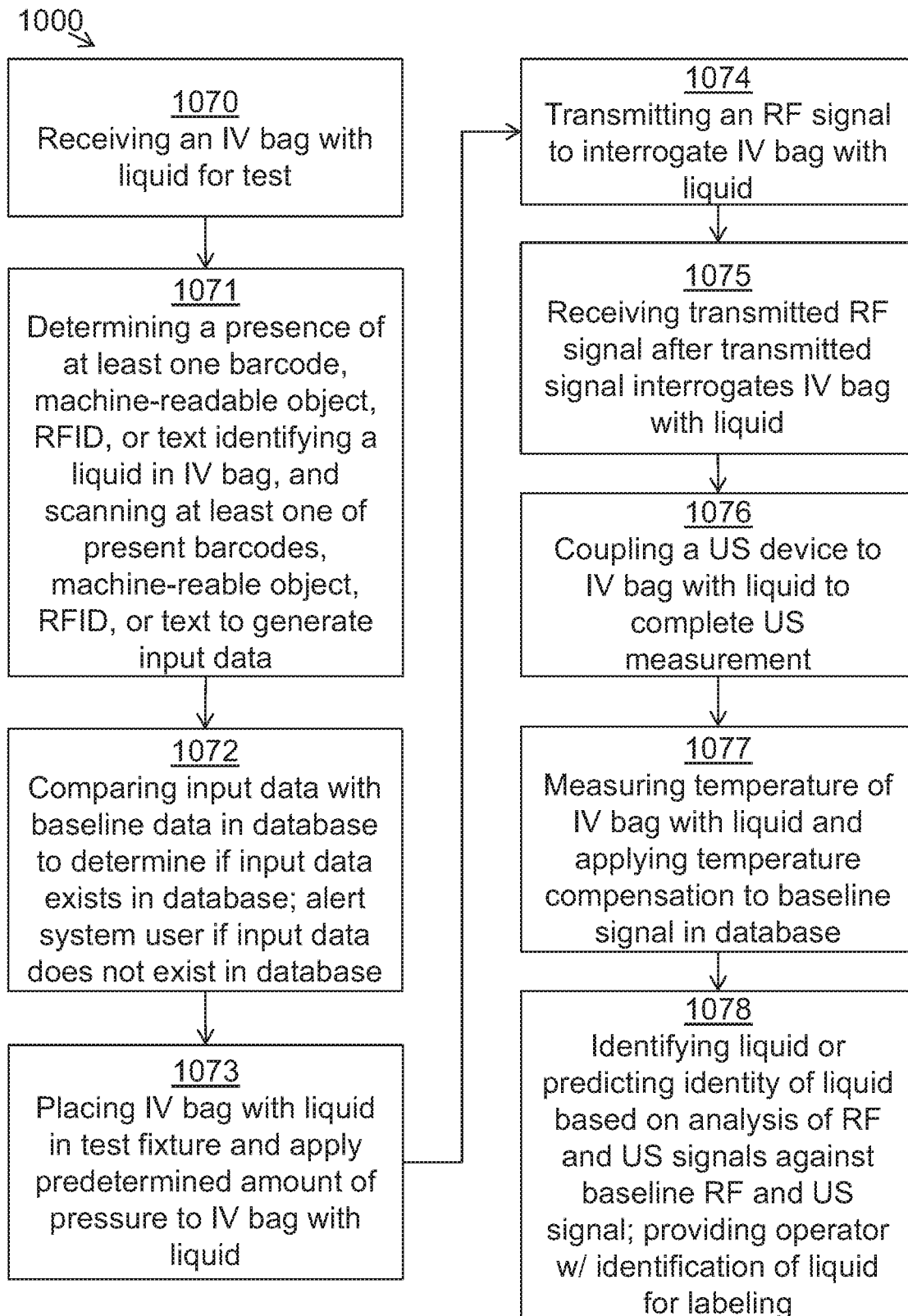
FIG. 10 illustrates a flow chart of an example method for using a liquid scanning system for IV drug verification and identification.

In addition to using US signal interrogation to identify a liquid, method 900 may include at least one of RF signal interrogation and US pulse echo interrogation. FIG. 10 is a flow chart of one embodiment of a method 1000 for verifying a drug and solution mixture contained in an intravenous (IV) bag. In one embodiment, method 1000 may include receiving a liquid-filled IV bag (1070). In one embodiment, method 1000 may also include determining a presence of at least one of a barcode, a machine-readable object, a radio frequency identification (RFID) tag, and text to identify a liquid in a liquid-filled IV bag, and scanning at least one present barcode, machine-readable object, RFID tag, and text to generate an input data (1071). In an absence of determining a presence of at least one of a barcode, a machine-readable object, a RFID tag, and a text in (1071), method 1000 may skip to step (1073). In one embodiment, method 1000 may also include comparing an input data with a baseline data in a database to determine if an input data exists in a database and alerting a user if an input data does not exists in a database (1072). In one embodiment, method 1000 may also include placing a liquid-filled IV bag in a test fixture and applying a predetermined amount of pressure to a liquid-filled IV bag in a test fixture (1073). In one embodiment, method 1000 may also include transmitting a RF signal to interrogate a liquid-filled IV bag in a test fixture (1074). In one embodiment, method 1000 may also include receiving a transmitted RF signal after a transmitted signal interrogates a liquid-filled IV bag in a test fixture (1075). In one embodiment, method 1000 may also include coupling an US device to a liquid-filled IV bag in a test fixture to complete an US measurement (1076). In one embodiment, method 1000 may also include measuring a temperature of a liquid-filled IV bag in a test fixture and applying a temperature compensation based on a measured temperature to all baseline RF signals and US measurements in a database (1077). In one embodiment, method 1000 may also include identifying a drug/solution mixture or predicting an identity of a drug/solution mixture based on an analysis of a received RF signal and US measurement against all baseline RF signals and US measurement in a database, and providing an operator an identification of a drug/solution mixture and printing or affixing at least one of a barcode, a machine-readable object, an RFID tag, and a text to a liquid-filled IV bag to indicate a content of a liquid-filled IV bag (1078). Identifying a content of a liquid-filled IV bag may include: identifying a liquid base of a liquid in an IV bag; identifying one or more drugs present in a liquid base; and identifying a concentration of one or more drugs in a liquid base. In a non-limiting example, an unknown liquid may be identified as lidocaine with a concentration of 2 mg/ml. In another non-limiting example, an unknown liquid may be identified as a saline solution with a concentration of 0.9%/1000 ml. In an alternative embodiment to (1078) of method 1000, a drug/solution mixture may not be identified by comparing received RF signal and US measurement against all baseline RF signals and US measurements in a database, and RF signals and US measurements of unidentified drug/solution mixture may be stored in a database for later identification. In an alternative embodiment to (1078) of method 1000, an identification of a drug/solution mixture may include outputting an identification of a drug/solution mixture to a display such as a computer monitor. Identification of a drug/solution mixture may include a name of a drug/solution mixture, a chemical representation of a drug/solution mixture, a concentration of a drug/solution mixture, and the like. Method 1000 may include interrogation and identification of a drug/solution mixture in other containers such as syringes, vials, bottles, and the like.

Any of the aforementioned systems and systems executing interrogation and identification methods described herein may further be networked to one another. A network may be a telecommunications network that may allow systems to communicate with each other and exchange data. Network links may be either wired or wireless, and nodes connecting systems to network links may be either wired or wireless. Networked systems may include software and hardware essential for networking—including, but not limited to one or more: modems, hubs, bridges, switches, host computers, routers, workstations, servers, and the like. In one embodiment, each system and system executing methods described herein has its own dedicated database. In another embodiment, a system and system executing methods described herein may share a remote database with one or more similar systems. Networked systems may interact with a hospital and pharmacy networks to allow for database updates, remote use of systems, and remote troubleshooting. For example, an unidentified liquid may be sent from a networked system to a remote, shared database and/or another system and be identified from a liquid signature already stored in the remote, shared database and/or other system. In another embodiment, a remote bar scanner scans a barcoded IV bag and sends the scanned barcode via a networked system to a database for identification of contents in a liquid-filled IV bag based on the scanned barcode.

Unless specifically stated to the contrary, the numerical parameters set forth in the specification, including the attached claims, are approximations that may vary depending on the desired properties sought to be obtained according to the exemplary embodiments. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Furthermore, while the systems, methods, and apparatuses have been illustrated by describing example embodiments, and while the example embodiments have been described and illustrated in considerable detail, it is not the intention of the applicants to restrict, or in any way limit, the scope of the appended claims to such detail. It is, of course, not possible to describe every conceivable combination of components or methodologies for purposes of describing the systems, methods, and apparatuses. With the benefit of this application, additional advantages and modifications will readily appear to those skilled in the art. Therefore, the invention, in its broader aspects, is not limited to the specific details and illustrative example and exemplary embodiments shown and described. Accordingly, departures may be made from such details without departing from the spirit or scope of the general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

As used in the specification and the claims, the singular forms "a," "an," and "the" include the plural. To the extent that the term "includes" or "including" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. Finally, where the term "about" is used in conjunction with a number, it is intended to include ±10% of the number. In other words, "about 10" may mean from 9 to 11.

Figure 11:
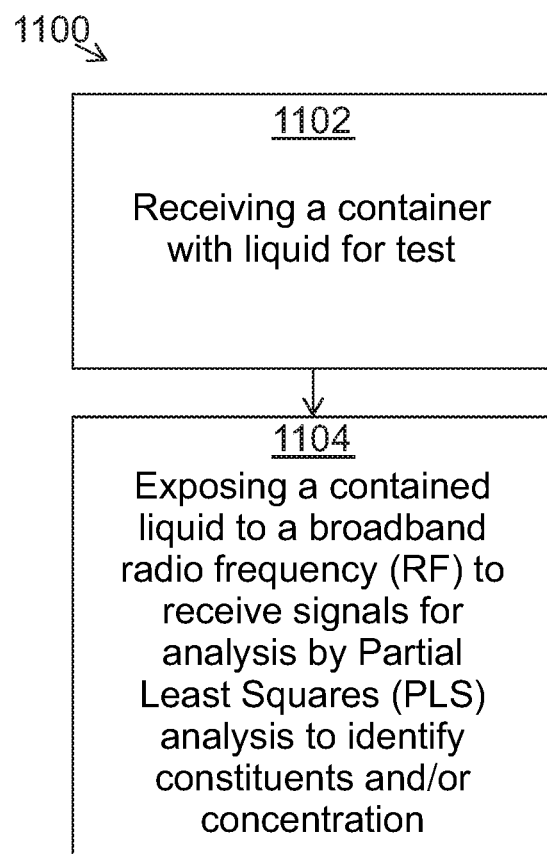
FIG. 11 illustrates a flow chart of an example method for solution constituent and/or concentration identification.

FIG. 11 illustrates a flow chart 1100 of an example method for constituent and/or concentration identification of solids dissolved in a solution. The liquid scanning system 100 may receive and/or be positioned near a container containing a solution for a test (1102). In some examples, the liquid scanning system 100 may identify a solution constituent and/or concentration using RF and Partial Least Squares (PLS) analysis. For example, the liquid scanning system 100 can identify the constituent and/or concentration of the solid dissolved in the solution by exposing a contained liquid to a broadband radio frequency (RF) pulse, receiving coupled and/or reflected return signals based on the exposing the contained liquid to the RF pulse, and analyzing the returned signals using PLS (1104). Some examples include identifying medications dissolved in IV bags and syringes, and/or identifying contents dissolved in liquids at security checkpoints.

Figure 12:
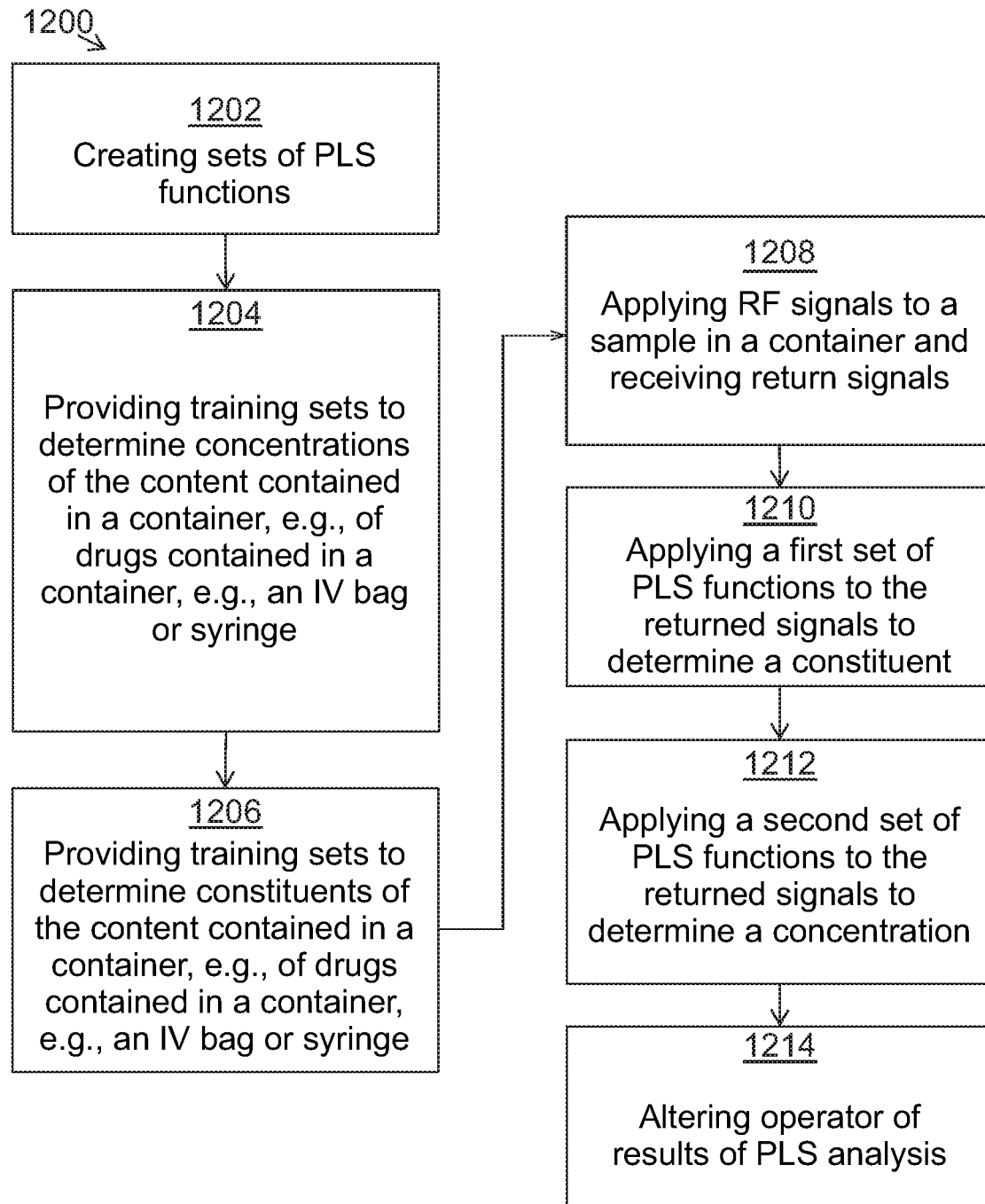
FIG. 12 illustrates a flow chart 1200 of an example method for solution constituent and/or concentration identification using RF and PLS.

FIG. 12 illustrates a flow chart 1200 of an example method for constituent and/or concentration identification of a solid dissolved in a solution, using RF and PLS. In some examples, the PLS analysis is implemented using a set of functions, e.g., one or more functions, to identify the constituents and/or concentration of the solution in a container. In some examples, a set of PLS functions can be created for each drug constituent and/or concentration, and then applied to all of the constituents and/or concentrations possible for the content of the solution contained in the container (1202). In some examples, the liquid scanning system 100 can provide training sets to help determine concentrations of the content contained in a container (1204). In some examples, the content is medicaments, e.g., drugs contained in IV bags, syringes and/or other types of containers. Training sets for concentration determination can be formulated in several ways, including but not limited to, by drug overall dosage ranges combined into a single training set, drugs broken into small ranges, drugs broken into adult and child dosages, etc. Additionally or alternatively, the liquid scanning system 100 can provide training sets to determine constituents of a content contained in the container, e.g., to determine drugs contained in an IV bag, syringe or other container (1206). In some examples, each drug dosage combination can require its own PLS function, and/or different container sets may require different PLS functions.

The liquid scanning system 100 can apply one or more RF signals to the content in the container and receive one or more RF signals based on the sent RF signals interacting with the content in the container (1208). For examples, transmitting and/or receiving of the RF signals may be accomplished using any of the transmitting and/or receiving antennas described above. To obtain accurate results, more than one PLS function, e.g., a first set of PLS functions, may be applied to the returned signals to determine a value for the constituent of the content in the container (1210). Additionally or alternatively, a second set of PLS functions may be applied to the returned signals to determine a value for the concentration of the content in the container (1212). In some examples, the constituent can be determined first and the concentration determined second, e.g., after determining the constituent to help better determine the PLS functions to use for determining the concentration. In other examples, the concentration may be determined before or at the same time as determining the constituent. In some examples, a first set of PLS functions is used to identify a drug present in a solution and a second set of PLS functions is used to identify the concentration of the drug. In other examples, a single PLS function, or single set of PLS functions, may be used to identify the drug and concentration. In some examples, the liquid scanning system 100 may compensate for temperature and maintain a constant pressure, constant path length, etc. during measurements of the return RF signal.

After PLS functions are determined they can be loaded onto the computer. The PLS functions can be used to return values to predict what drug and concentration of the drug are present in the liquid. For comparison purposes, the liquid scanning system 100 may use a signal received with no drug or other content present as a baseline signal. When a sample (IV bag, syringe, etc.) is placed on the system the RF signal at the receiving antenna has been altered. The liquid scanning system 100 may compare the altered return RF signal to the baseline signal in time domain and frequency domain. In some examples, the liquid scanning system 100 may calculate ratio and differences of FFT analysis. Additional features may also be calculated, e.g., number of peaks, location of peaks, shape of peaks, amplitude of peaks, etc. In some examples, the liquid scanning system 100 can input the temperature and/or additional features into the PLS analysis. In some examples, additional inputs may include ultrasonic velocity readings. In some examples, the liquid scanning system 100 can alert an operator to the results of the analysis, e.g., the constituent and/or concentration of the content (1214).

Figure 13:
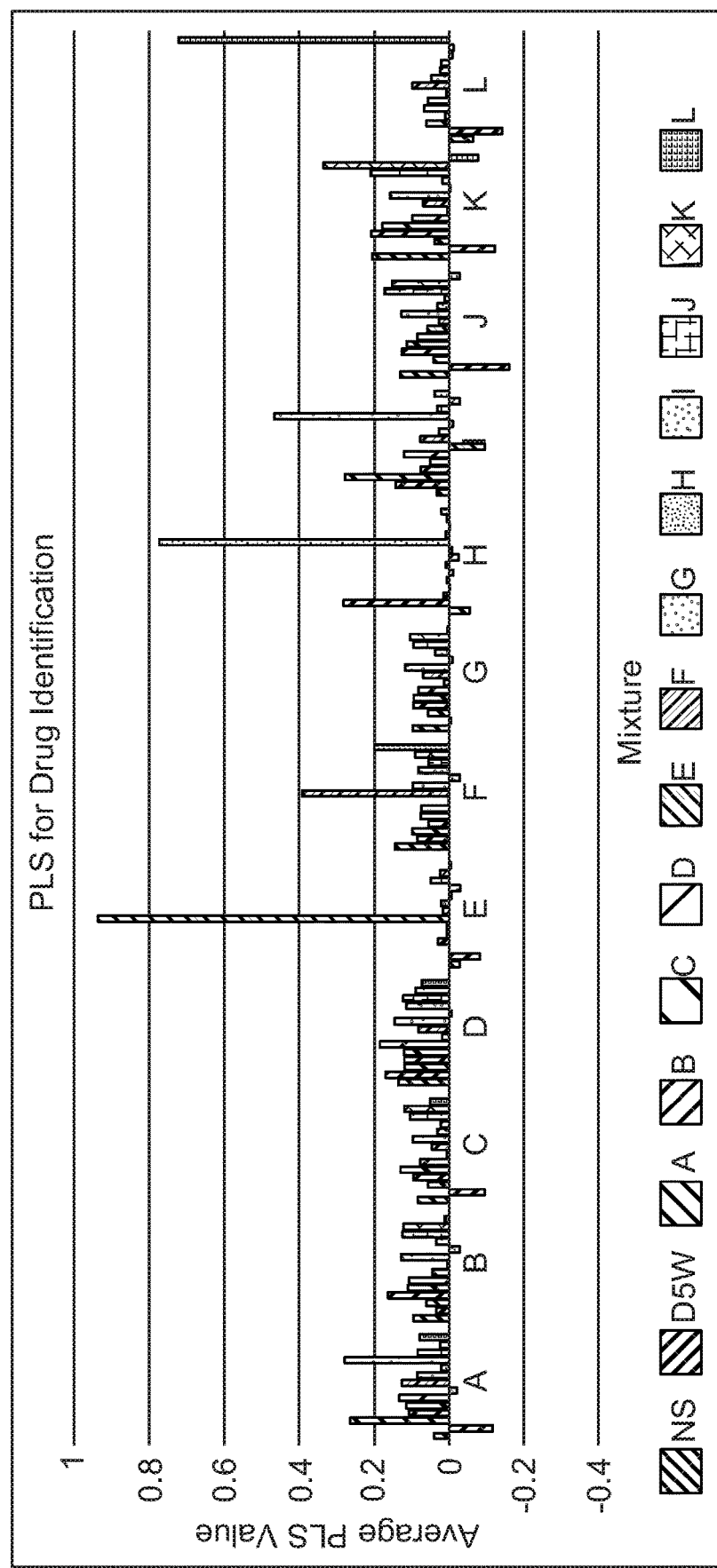
FIG. 13 is a graph of example constituent identification using RF and PLS.

FIG. 13 is a graph 1300 of example constituent identification using RF and PLS. In some examples, the liquid scanning system 100 can analyze a series of known variables to develop PLS functions to identify the components of sample, e.g., samples A-L. The liquid scanning system 100 then uses the functions to predict future behavior of scanned samples, e.g., to identify constituents and/or concentrations for the sample. In an example test, concentrations containing a particular drug are set to a value of one (1). Other drug combinations can be set to zero (0). The liquid scanning system 100 trains a percentage of the RF scans to develop functions to test on the remaining data. The PLS technique may be used to create a predictive model for each of the samples tested. In some examples, the liquid scanning system 100 can identify amounts of about 10 µg/ml or less.

Figure 14:
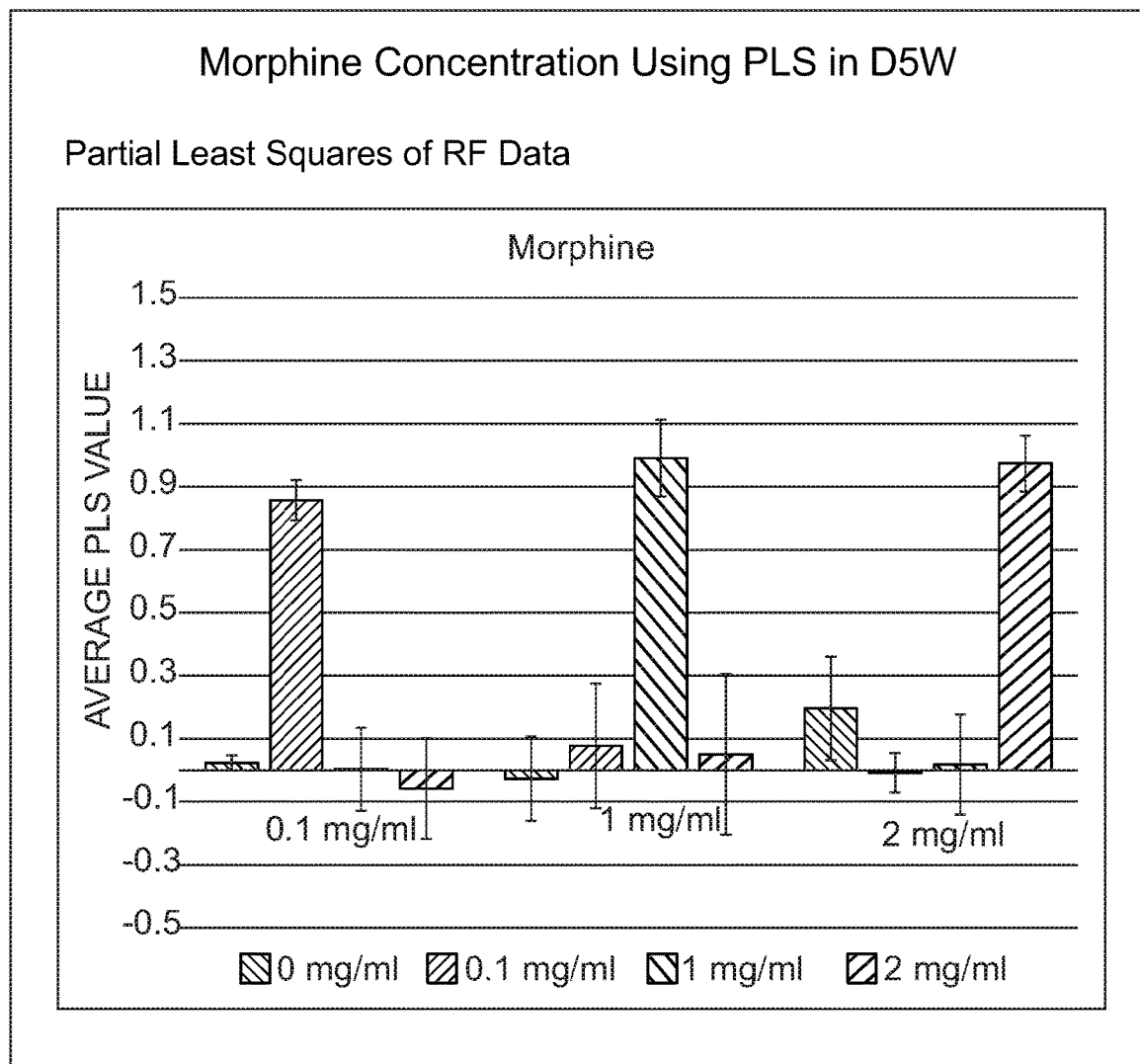
FIG. 14 is a graph of example PLS values for each measurement averaged to determine a value for the drug.

FIG. 14 is a graph of example PLS values for each measurement averaged to determine a value for the drug. In some examples, the highest value average can be used to identify the drug. FIG. 15 is a chart of example averages for drugs using RF and PLS to identify the constituent of a solution, e.g., the drug. Additional data can be collected to reduce any variance of the PLS technique, e.g., temperature, container placement, container thickness, sensor repeatability and/or measurement repeatability, and/or to give a bigger data set and more confidence in results. In some examples, a PLS function can be created for each drug concentration and then applied to all of the concentrations for the same drug. Using the PLS technique on the RF signal can be used to obtain good concentration data, even in the cases where ultrasound cannot measure a concentration difference.

While various embodiments have been described, it can be apparent that many more embodiments and implementations are possible. Accordingly, the embodiments are not to be restricted.

What is claimed is:

1. A method of identifying a constituent and a concentration of a solid dissolved in a solution contained in a container, comprising:
providing an input radio frequency (RF) signal to the solution; receiving at least one of a reflected RF signal and a coupled RF signal; analyzing the received RF signal in at least one of a frequency domain and a time domain for a measurement to which a Partial Least Squares (PLS) regression has been applied;
applying a first set of PLS functions to the received RF signal to determine a value of a constituent of the solid dissolved in the solution;
applying a second set of PLS functions to the RF signal to determine a value of a concentration of the solid dissolved in the solution;

comparing the value of the constituent and the value of the concentration of the solid dissolved in the solution against one or more baseline measurements in a database;

where the comparing further comprises comparing one or more of a number of peaks, location of peaks, shape of peaks and amplitude of peaks; and identifying the constituent and the concentration of the solid dissolved in the solution from the compared measurements.

2. The method of claim 1, wherein identifying the constituent and the concentration of the solid dissolved in the solution comprises identifying a drug/solution mixture contained in the container.

3. The method of claim 2, further comprising creating a set of PLS functions for each drug concentration.

4. The method of claim 3, where the first set of PLS functions to identify the constituent and the second set of PLS functions to identify the concentration are the different.

5. The method of claim 3, where a single set of PLS function identifies the constituent and the concentration.

6. The method of claim 1, wherein the container comprises at least one of an intravenous (IV) bag and a syringe.

7. The method of claim 1, where the value of the concentration comprises an average of a plurality of values.

8. The method of claim 1, where the value of the constituent comprises an average of a plurality of values.

9. The method of claim 1, where the first set of PLS functions is formulated for at least one of solids over all dosage ranges combined into a single training set, solids broken into small ranges, solids broken into a first dosage and a second dosage, and each solid dosage combination including a PLS function.

10. An apparatus for identifying the identity of a liquid sample in a container, comprising:
   a radio frequency (RF) signal generator producing an RF frequency between 100 MHz and 15 GHz positioned to interrogate a liquid sample contained in a container;
   a receiver positioned to receive at least one of a reflected RF signal and a coupled RF signal;
   a processor for processing at least one of the received RF signals, the processor programmed to:
   analyze the received RF signal in at least one of a frequency domain and a time domain for a measurement to which a Partial Least Squares (PLS) regression has been applied;
   apply a first set of PLS functions to the received RF signal to determine a value of a constituent of the solid dissolved in the solution;
   apply a second set of PLS functions to the RF signal to determine a value of a concentration of the solid dissolved in the solution;
   compare the value of the constituent and the value of the concentration of the solid dissolved in the solution against one or more baseline measurements in a database;
   where the comparing further comprises comparing one or more of a number of peaks, location of peaks, shape of peaks and amplitude of peaks; and
   identify the constituent and the concentration of the solid dissolved in the solution from the compared measurements.

11. The apparatus of claim 10, wherein identifying the constituent and the concentration of the solid dissolved in the solution comprises identifying a drug/solution mixture contained in the container.

12. The apparatus of claim 11, further comprising creating a set of PLS functions for each drug concentration.

13. The apparatus of claim 12, where the first set of PLS functions to identify the constituent and the second set of PLS functions to identify the concentration are the different.

14. The apparatus of claim 12, where a single set of PLS function identifies the constituent and the concentration.

15. The apparatus of claim 10, wherein the container comprises at least one of an intravenous (IV) bag and a syringe.

16. The apparatus of claim 10, where the value of the concentration comprises an average of a plurality of values.

17. The apparatus of claim 10, where the value of the constituent comprises an average of a plurality of values.

18. The apparatus of claim 10, where the first set of PLS functions is formulated for at least one of solids over all dosage ranges combined into a single training set, solids broken into small ranges, solids broken into a first dosage and a second dosage, and each solid dosage combination including a PLS function.

* * * * *